(12) United States Patent
Shal et al.

(10) Patent No.: US 11,344,670 B2
(45) Date of Patent: May 31, 2022

(54) SMALL NON-ELECTRICALLY DRIVEN PORTABLE INFUSION DEVICE

(71) Applicants: Mark Shal, Laguna Niguel, CA (US); Kurt Sebesta, Chonburi (TH)

(72) Inventors: Mark Shal, Laguna Niguel, CA (US); Kurt Sebesta, Chonburi (TH)

( * ) Notice: Subject to any disclaimer, the term of this patent is extended or adjusted under 35 U.S.C. 154(b) by 441 days.

(21) Appl. No.: 16/591,817

(22) Filed: Oct. 3, 2019

(65) Prior Publication Data

US 2021/0100949 A1 Apr. 8, 2021

(51) Int. Cl.
*A61M 5/142* (2006.01)
*A61M 39/02* (2006.01)
*A61M 5/145* (2006.01)

(52) U.S. Cl.
CPC .... *A61M 5/14244* (2013.01); *A61M 39/0247* (2013.01); *A61M 2005/14506* (2013.01); *A61M 2039/0297* (2013.01)

(58) Field of Classification Search
CPC ........... A61M 2005/14506; A61M 2039/0297; A61M 39/0247; A61M 5/14244; A61M 5/14586; A61M 5/14593; A61M 5/148; A61M 5/1483; A61M 5/1486; A61M 5/152; A61M 5/155

See application file for complete search history.

(56) References Cited

U.S. PATENT DOCUMENTS

| | | | | |
|---|---|---|---|---|
| 3,412,906 A | * | 11/1968 | Dinger | A61M 5/152 141/318 |
| 4,769,008 A | * | 9/1988 | Hessel | A61M 5/152 222/211 |
| 4,953,753 A | * | 9/1990 | Gortz | B65D 83/0061 222/105 |
| 5,284,481 A | * | 2/1994 | Soika | A61M 5/152 206/370 |
| 5,433,709 A | * | 7/1995 | Kriesel | A61M 5/152 604/132 |
| 5,529,214 A | * | 6/1996 | Lasonde | B65D 83/0061 222/105 |
| 7,322,961 B2 | * | 1/2008 | Forrest | A61M 5/152 604/93.01 |
| 2006/0229558 A1 | * | 10/2006 | Heston | A61M 5/152 604/131 |
| 2019/0366002 A1 | * | 12/2019 | Verlaak | A61M 5/1486 |
| 2019/0388613 A1 | * | 12/2019 | Aurin | A61M 5/152 |

* cited by examiner

*Primary Examiner* — Quynh-Nhu H. Vu
(74) *Attorney, Agent, or Firm* — Michael M. Ahmadshahi (57) ABSTRACT

An infusion pump includes a core member and a bladder member which are substantially spheroidal at one end and cylindrical at the other end. The core member is inserted inside the bladder member and a ring member engages the cylindrical ends of the core and bladder member to sealingly secure the bladder to the core. A tubular hose is included and is coupled with an infusion port of the core member. When fluid is injected into the pump, it causes the bladder member to inflate substantially symmetrically and spherically around an axial axis of the core member. Upon deflating the bladder member, the fluid is ejected out of the pump at a constant flow rate.

17 Claims, 6 Drawing Sheets

SMALL NON-ELECTRICALLY DRIVEN PORTABLE INFUSION DEVICE

COPYRIGHT

A portion of the disclosure of this patent document contains material which is subject to copyright protection. The owner has no objection to the facsimile reproduction by anyone of the patent disclosure, as it appears in the Patent and Trademark Office files or records, but otherwise reserves all copyright rights whatsoever.

FIELD OF INVENTION

The present invention relates to an infusion pump including method of operation, wherein the pump includes a core and a bladder which are substantially spheroidal at one end and cylindrical at the other end. The core is disposed inside the bladder and a ring is included to engage the cylindrical ends of the core and bladder in order to sealingly secure the bladder to the core. A tubular hose is included and is coupled with an infusion port of the core member whereby a fluid can be injected into the pump causing the bladder member to inflate substantially symmetrically around an axial axis of the core member, and subsequently ejected from the pump at a constant flow rate.

BACKGROUND

Conventional infusion pumps have encountered problems such as leakage, inaccurate flow rates, and lack of ergonomics in design. For instance, the conventional pump includes a bladder that are multilayers and lack symmetry when inflated. Furthermore, the bladder has two open ends which must be sealed at both ends, thereby, increasing the chances of leakage. The infusion tubes of the conventional pumps have small diameters which makes it difficult for the user to inject liquid inside the pump.

The present invention is a small non-electrically driven portable elastomeric infusion pump that is intended for patients requiring intravenous, percutaneous, subcutaneous, intra-operative sites or epidural administration of medications. The user is responsible to ensure that the medication is prepared and administered in accordance with the drug manufacturers package insert.

The pump delivers controlled amounts of medication directly to the intra-operative site for pain management and or antibiotic administration. The pump infuses medication at an hourly flow rate (m/h). Medications are infused intra-operatively and postoperatively through intramuscular or subcutaneous routes. The pump is also intended for controlled delivery of local anesthetics in close proximity to nerves for postoperative regional anesthesia and pain management. Route of administration includes intra-operative or percutaneous. The pump is ethylene oxide (EO) sterilized and single use disposable. As mentioned above, the versatile use of the pump includes antibiotic therapy, chemotherapy, and pain management. The user-friendly pump features easy filling, well labeled, and color coding.

SUMMARY

In one aspect, an infusion pump is disclosed, wherein the pump comprises a core member comprising a substantially spheroidal first distal core-end, a substantially cylindrical second distal core-end, and an infusion port, a substantially tubular bladder member comprising a substantially spheroidal first distal bladder-end, and a substantially cylindrical open second distal bladder-end operative to receive the core member, wherein the core member is disposed inside the bladder member, a ring member operative to engage the second distal core-end and the second distal bladder-end to sealingly secure the bladder member to the core member, and a substantially tubular hose comprising a first distal hose-end and a second distal hose-end, wherein the first distal hose-end is coupled with the infusion port, whereby injecting a fluid into the infusion pump via the tubular hose inflates the bladder member and stores the fluid substantially symmetrically within the bladder member and the core member around an axial axis of the core member, and whereby allowing the bladder member to deflate ejects the fluid out of the infusion pump via the tubular hose at a substantially constant flow rate.

Preferably, the bladder member inflates into a substantially spherical shape when the fluid is stored within the bladder member and the core member.

Preferably, the core member is made from a rigid plastic material.

Preferably, the bladder member is made from an elastomeric material.

Preferably, the tubular hose is coupled with the infusion port via an adhesive.

Preferably, an inner diameter of the tubular hose is greater than 2.2 millimeters.

Preferably, the second distal core-end comprises a first core-flange and wherein the second distal bladder-end comprises a bladder-shoulder operative to engage the first core-flange.

Preferably, the second distal core-end comprises a second core-flange, wherein the ring member comprises a first distal ring-end and a second distal ring-end, and wherein the second distal ring-end compressively abuts the second core-flange thereby applying a compressive force, via the first distal ring-end, on the bladder-shoulder to further sealingly secure the bladder member to the core member.

Preferably, the first distal ring-end comprises a ring-shoulder operative to engage the bladder-shoulder to further sealingly secure the bladder member to the core member.

Preferably, the pump further comprises a cap, wherein the second distal core-end comprises a third core-flange, and wherein the cap comprises a first cap-flange operative to engage the third core-flange.

Preferably, the pump further comprises a connector tube wherein the connector tube comprises a check valve, a first distal tube-end, and a second distal tube-end, wherein the first distal tube-end is releasably coupled with the second distal hose-end.

Preferably, the pump further comprises a protective cover enveloping the bladder member.

In another aspect, an infusion pump is disclosed, wherein the pump comprises a core member comprising a substantially spheroidal first distal core-end, and an infusion port, a substantially tubular bladder member comprising a substantially spheroidal first distal bladder-end, wherein the core member is disposed inside the bladder member, and a ring member operative to sealingly secure the bladder member to the core member, wherein a fluid, injected through the infusion port, is stored substantially symmetrically within the bladder member and the core member around an axial axis of the core member, and is ejected through the infusion port at a substantially constant flow rate.

Preferably, the bladder member inflates into a substantially spherical shape when the fluid is stored within the bladder member and the core member.

Preferably, the core member is made from a rigid plastic material.

Preferably, the bladder member is made from an elastomeric material.

In another aspect, a method of injecting, storing, and ejecting a fluid via an infusion pump is disclosed wherein the method comprises providing a core member comprising a substantially spheroidal first distal core-end, a substantially cylindrical second distal core-end, and an infusion port, providing a substantially tubular bladder member comprising a substantially spheroidal first distal bladder-end, and a substantially cylindrical open second distal bladder-end operative to receive the core member, wherein the core member is disposed inside the bladder member, providing a ring member operative to engage the second distal core-end and the second distal bladder-end to sealingly secure the bladder member to the core member, and providing a substantially tubular hose comprising a first distal hose-end and a second distal hose-end, wherein the first distal hose-end is coupled with the infusion port, whereby injecting a fluid into the infusion pump via the tubular hose inflates the bladder member and stores the fluid substantially symmetrically within the bladder member and the core member around an axial axis of the core member, and whereby allowing the bladder member to deflate ejects the fluid out of the infusion pump via the tubular hose at a substantially constant flow rate.

Preferably, the bladder member inflates into a substantially spherical shape when the fluid is stored within the bladder member and the core member.

Preferably, the method further comprises providing a cap, wherein the second distal core-end comprises a third core-flange, and wherein the cap comprises a first cap-flange operative to engage the third core-flange.

Preferably, the method further comprises providing a connector tube wherein the connector tube comprises a check valve, a first distal tube-end, and a second distal tube-end, wherein the first distal tube-end is releasably coupled with the second distal hose-end.

Preferably, the method further comprises providing a protective cover enveloping the bladder member.

In another aspect, a method of injecting, storing, and ejecting a fluid via an infusion pump is disclosed, wherein the method comprises providing a core member comprising a substantially spheroidal first distal core-end, and an infusion port, providing a substantially tubular bladder member comprising a substantially spheroidal first distal bladder-end, wherein the core member is disposed inside the bladder member, and providing a ring member operative to sealingly secure the bladder member to the core member, wherein the fluid, injected through the infusion port, is stored substantially symmetrically within the bladder member and the core member around an axial axis of the core member, and is ejected through the infusion port at a substantially constant flow rate.

Preferably, the bladder member inflates into a substantially spherical shape when the fluid is stored within the bladder member and the core member.

Preferably, the core member is made from a rigid plastic material.

Preferably, the bladder member is made from an elastomeric material.

DETAILED DESCRIPTION OF THE PRESENTLY PREFERRED EMBODIMENTS

Figure 1:
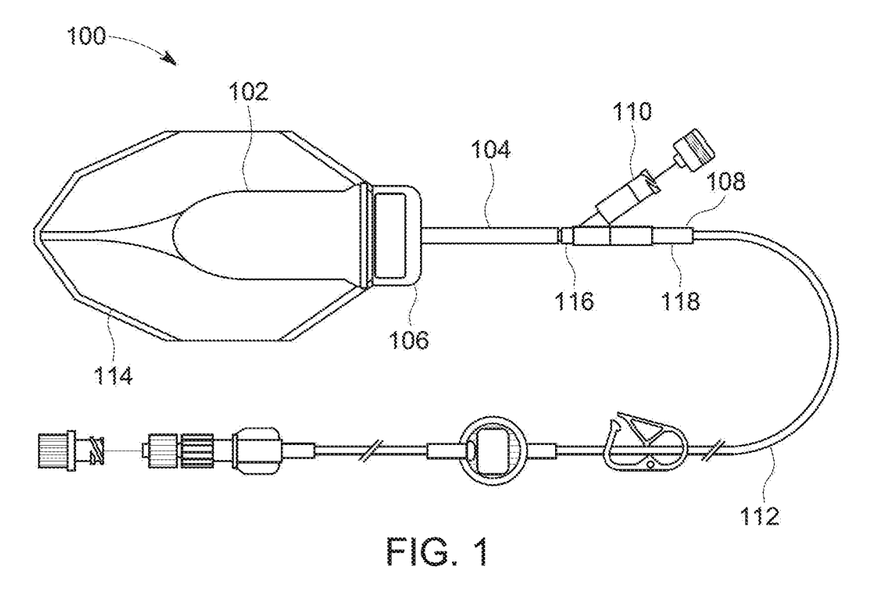
FIG. 1 shows a side view of an infusion pump, according to a preferred embodiment.

FIG. 1 depicts a side view 100 of an infusion pump and other components that may be connected to the infusion pump's tubular hose. According to this preferred embodiment, the infusion pump includes a bladder member 102, a core member (not visible in this figure) inside the bladder member 102, a cap 106, a tubular hose 104, a protective cover 114, a connector tube 108 having a first distal tube-end 116, a second distal tube-end 118, and a check valve 110. The second distal tube-end 118 is further connected to other components 112 which are used to infuse a liquid in a human's body.

Figure 2:
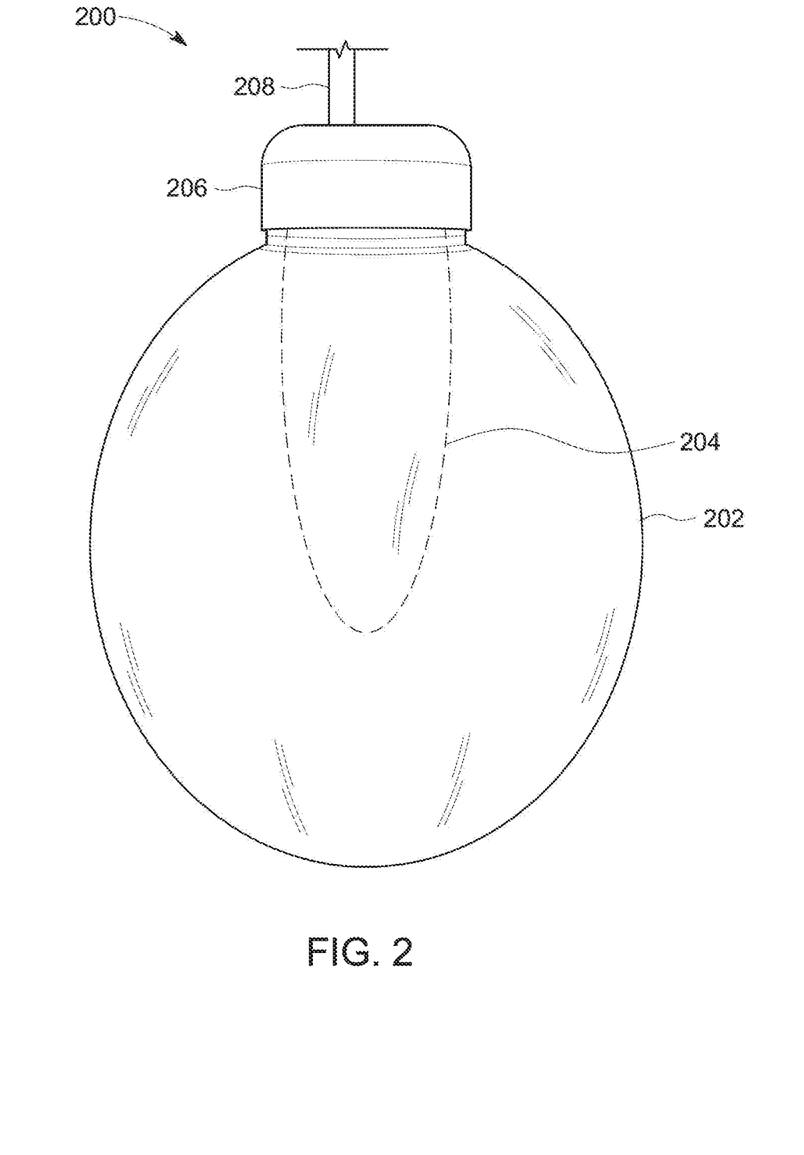
FIG. 2 shows a perspective view of an infusion pump illustrating the substantially spherical symmetrical inflation of the bladder member over the core member, according to a preferred embodiment.

FIG. 2 depicts a perspective view of an infusion pump 200 comprising a core member 204, a substantially tubular bladder member 202, a ring member (not visible in this figure), a substantially tubular hose 208, and a cap 206, according to a preferred embodiment. The tubular hose 208 is coupled with an infusion port (not visible in this figure) of the core member 204 and it is used to inject and eject a fluid into and out of the infusion pump 200.

Figure 5A:
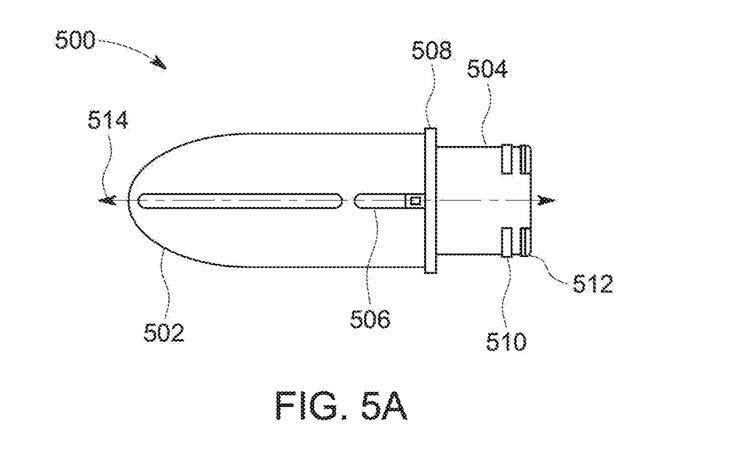
FIG. 5A shows a side view of a core member of an infusion pump, according to a preferred embodiment.
Figure 5B:
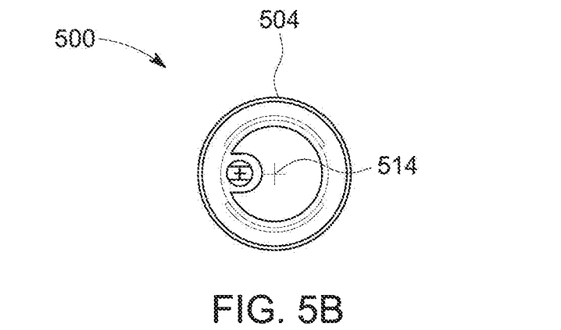
FIG. 5B shows a front view of the core member of FIG. 5A.

The core member 204 includes a substantially spheroidal first distal core-end, a substantially cylindrical second distal core-end, and an infusion port which are shown in detail in FIG. 5A and FIG. 5B. The bladder member 202 is substantially tubular and it includes a substantially spheroidal first distal bladder-end and a substantially cylindrical open second distal bladder-end. The second distal bladder-end of the bladder member 202 is open and it operates to receive the core member 204 inside the bladder member 202. The ring member, shown in detail in FIG. 6A, FIG. 6B, and FIG. 6C, operates to engage the second distal core-end and the second distal bladder-end. The ring member is used to seal and secure the bladder member 202 to the core member 204. The hose 208 is substantially tubular and it includes a first distal hose-end and a second distal hose-end. The tubular hose 208 is coupled with the infusion port of the core member 204 via the first distal hose-end. The cap 206 includes a cap-flange that engages a core-flange to further seal and secure the bladder member 202 to the core member 204. The cap 206 further operates to retain a protective cover (not shown in this figure), such as the protective cover 114 shown in FIG. 1.

As can be seen in this FIG. 2, a fluid has been injected into the infusion pump 200 via the tubular hose 208 inflating the bladder member 202 and storing the fluid substantially symmetrically within the bladder member 202 and the core member 204 around an axial axis of the core member 204. By allowing the bladder member 202 to deflate, the fluid is ejected out of the infusion pump 200 via the tubular hose 208 at a substantially constant flow rate.

Figure 3:
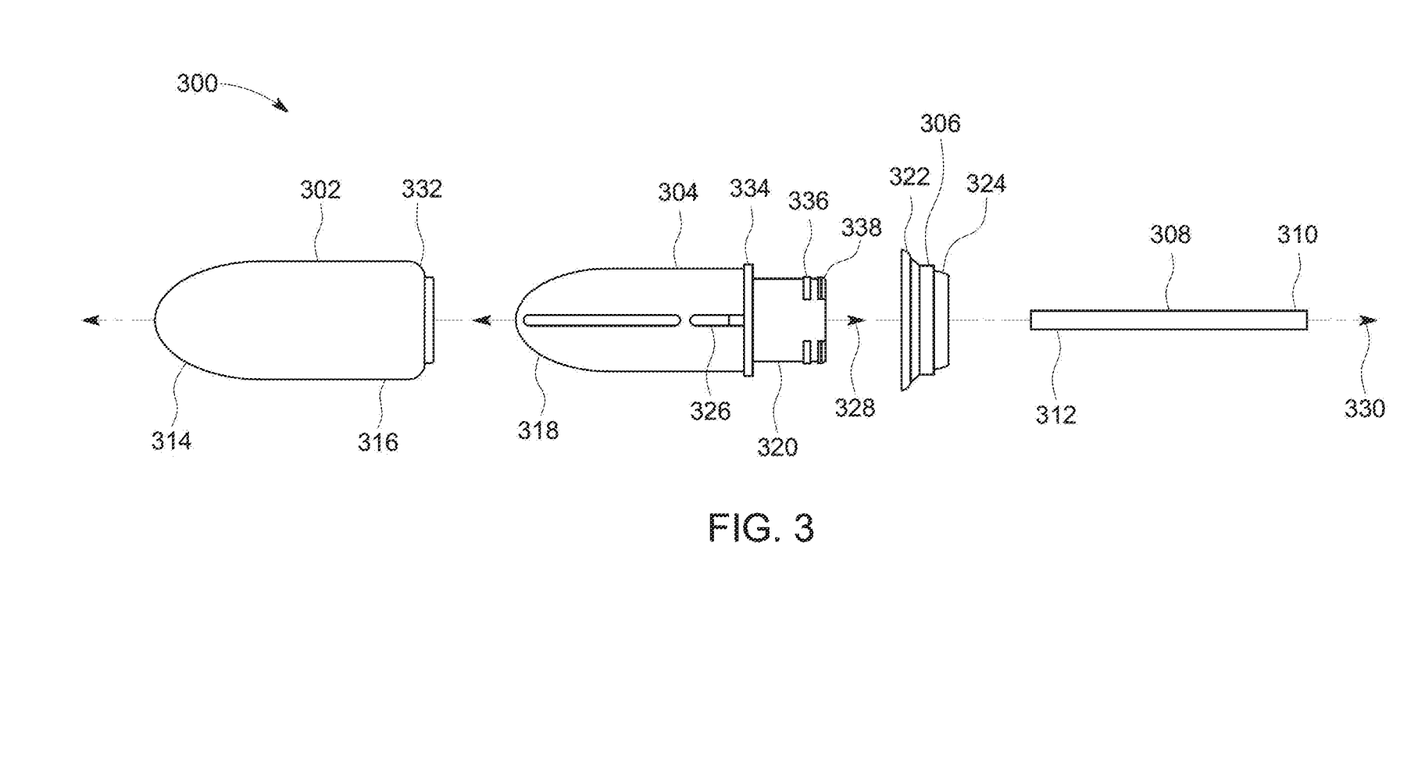
FIG. 3 shows an exploded side view of an infusion pump, according to a preferred embodiment.

FIG. 3 depicts an exploded side view of an infusion pump 300, according to a preferred embodiment. The pump 300 comprises a core member 304 comprising a substantially spheroidal first distal core-end 318, a substantially cylindrical second distal core-end 320 and an infusion port 326. The pump 300 further comprises a substantially tubular bladder member 302 comprising a substantially spheroidal first distal bladder-end 314 and a substantially cylindrical open second distal bladder-end 316 which operates to receive the core member 304. As such, the core member 304 is disposed inside the bladder member 302. According to this preferred embodiment, the bladder member 302 is tubular and open at one end, whereas the core member 304 is solid and closed at both ends. The second distal core-end 320 comprises a first core-flange 334 and the second distal bladder-end 316 comprises a bladder-shoulder 332. Once the core member 304 is disposed inside the bladder member 302, the bladder-shoulder 332 engages the first core-flange 334.

The pump 300 further comprises a ring member 306 which is used to engage the second distal core-end 320 and the second distal bladder-end 316 to sealingly secure the bladder member 302 to the core member 304. The ring member 306 includes a first distal ring-end 322 and a second distal ring-end 324. The second distal core-end 320 comprises a second core-flange 336, the second distal ring-end 324 compressively abuts the second core-flange 336, thereby, applying a compressive force, via the first distal ring-end 322 on the bladder-shoulder 332 to further sealingly secure the bladder member 302 to the core member 304.

The pump 300 further comprises a substantially tubular hose 308 comprising a first distal hose-end 312 and a second distal hose-end 310. The first distal hose-end 312 is coupled with the infusion port 326. When a fluid is injected into the infusion pump 300 via the tubular hose 308, it causes the bladder member 302 to inflate and store the fluid substantially symmetrically within the bladder member 302 and the core member 304 around an axial axis of the core member 328. In a preferred embodiment, the bladder member 302 inflates into a substantially spherical shape when the fluid is stored within the bladder member 302 and the core member 304. When the bladder member 302 deflates, the fluid is ejected out of the infusion pump 300 via the tubular hose 308 at a substantially constant flow rate. In a preferred embodiment, an inner diameter of the hose 308 is greater than 2.2 millimeters.

Figure 4A:
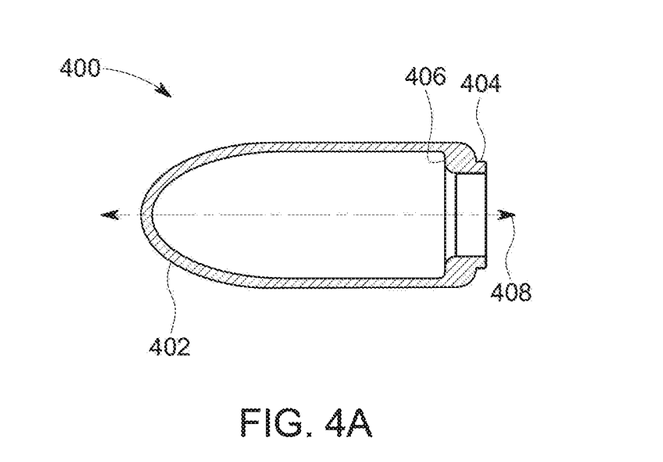
FIG. 4A shows a side cross-sectional view of a bladder member of an infusion pump, according to a preferred embodiment.
Figure 4B:
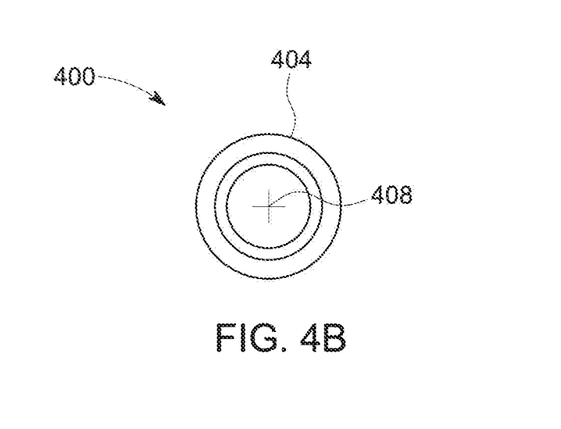
FIG. 4B shows a front view of the bladder member of FIG. 4A.

FIG. 4A depicts a side cross-sectional view of a bladder member 400 of an infusion pump, according to a preferred embodiment. The bladder member 400 is substantially tubular and it includes a substantially spheroidal first distal bladder-end 402 and a substantially cylindrical open second distal bladder-end 404. A core member, such as the core member 304 shown in FIG. 3, is inserted into the open second distal bladder-end 404 which operates to receive the core member 304. Accordingly, the core member 304 would be disposed inside the bladder member 400 and its axial axis 328 would be coincidental with an axial axis 408 of the bladder 400. The bladder member 400 includes a bladder-shoulder 406 which is used to engage the core member 304 via the first core-flange 334. In a preferred embodiment, the bladder member 400 is made from an elastomeric material. FIG. 4B depicts a front view of the bladder member 400 of FIG. 4A, further showing the substantially cylindrical open second distal bladder-end 404 and the axial axis 408 of the bladder member 400.

FIG. 5A depicts a side view of a core member 500 of an infusion pump, according to a preferred embodiment. The core member 500 includes a substantially spheroidal first distal core-end 502, a substantially cylindrical second distal core-end 504, and an infusion port 506. The infusion port 506 is circular in shape, as shown in FIG. 5B, on the front side of the core member 500 and has a slit shape, as shown in FIG. 5A, on the left side of the core member 500. A first distal hose-end, such as the first distal hose-end 312 of the hose 308 as shown in FIG. 3, is coupled with the circular end of the infusion port 506, preferably by utilizing an adhesive. Fluid is injected into the pump via the hose 308 and comes out of the slit side of the infusion port 506 and into a bladder member, such as the bladder member 400 shown in FIG. 4A and FIG. 4B.

The fluid is stored within the bladder member 400 and the core member 500. In a preferred embodiment, the bladder member 400 is inflated into a substantially spherical shape and positioned substantially symmetrically around an axial axis 514 of the core member 500. The second distal core-end 504 comprises a first core-flange 508. The bladder-shoulder 406 of the bladder member 400 would operate to engage the first core-flange 508.

In a preferred embodiment, the second distal core-end 504 further comprises a second core-flange 510 which would be used by a ring-end, such as the second distal ring-end 324 of the ring member 306 shown in FIG. 3. The second distal ring-end 324 and a second distal ring-end would compressively abut the second core-flange 510 thereby applying a compressive force, via the first distal ring-end 322, on the bladder-shoulder 406 to further sealingly secure the bladder member 400 to the core member 500.

In a preferred embodiment, the second distal core-end 504 further comprises a third core-flange 512 which could be used to engage a cap-flange (not shown) of a cap (not shown), such as the cap 106 shown in FIG. 1. The cap 106 in FIG. 1 further operates to retain the protective cover 114. In a preferred embodiment, the core member 500 is made from a rigid plastic material.

Figure 6A:
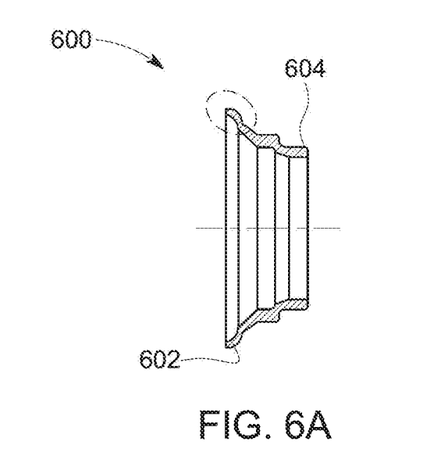
FIG. 6A shows a side cross-sectional view of a ring member of an infusion pump, according to a preferred embodiment.
Figure 6B:
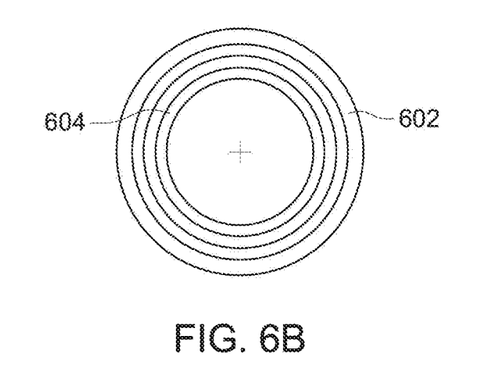
FIG. 6B shows a front view of the ring member of FIG. 6A.
Figure 6C:
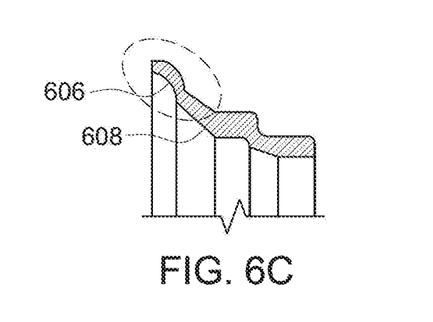
FIG. 6C shows a side partial cross-sectional view the ring member of FIG. 6A.

FIGS. 6A, 6B, and 6C depict a side cross-sectional view, a front view, and a side partial cross-sectional view, respectively, of a ring member 600 of an infusion pump, according to a preferred embodiment. The ring member 600 comprises a first distal ring-end 602 and a second distal ring-end 604. The second distal ring-end 604 compressively abuts a core flange, such as the second core-flange 510 of the core member 500 shown in FIG. 5A and FIG. 5B, and by doing so, it applies a compressive force through a chamfered annular surface 608 of its first distal ring-end 602 on a bladder shoulder, such as the bladder-shoulder 406 of the bladder member 400 shown in FIG. 4 A and FIG. 4B, to further sealingly secure the bladder member 400 to the core member 500. In this preferred embodiment, the first distal ring-end 602 of the ring member 600 comprises a ring-shoulder 606 which operates to engage the bladder-shoulder 406 of the bladder member 400 to further sealingly secure the bladder member 400 to the core member 500.

The foregoing explanations, descriptions, illustrations, examples, and discussions have been set forth to assist the reader with understanding this invention and further to demonstrate the utility and novelty of it and are by no means restrictive of the scope of the invention. It is the following claims, including all equivalents, which are intended to define the scope of this invention.

What is claimed is:

1. An infusion pump, comprising:
   (a) a core member comprising:
   (i) a substantially spheroidal first distal core-end;
   (ii) a substantially cylindrical second distal core-end; and
   (iii) an infusion port;
   (b) a substantially tubular bladder member comprising:
   (i) a substantially spheroidal first distal bladder-end; and
   (ii) a substantially cylindrical open second distal bladder-end operative to receive the core member;
   wherein the core member is disposed inside the bladder member;
   (c) a ring member operative to engage the second distal core-end and the second distal bladder-end to sealingly secure the bladder member to the core member; and
   (d) a substantially tubular hose comprising a first distal hose-end and a second distal hose-end, wherein the first distal hose-end is coupled with the infusion port;
   whereby injecting a fluid into the infusion pump via the tubular hose inflates the bladder member and stores the fluid substantially symmetrically within the bladder member and the core member around an axial axis of the core member; and
   whereby allowing the bladder member to deflate ejects the fluid out of the infusion pump via the tubular hose at a substantially constant flow rate.

2. The infusion pump of claim 1, wherein the bladder member inflates into a substantially spherical shape when the fluid is stored within the bladder member and the core member.

3. The infusion pump of claim 1, wherein the core member is made from a rigid plastic material.

4. The infusion pump of claim 1, wherein the bladder member is made from an elastomeric material.

5. The infusion pump of claim 1, wherein the tubular hose is coupled with the infusion port via an adhesive.

6. The infusion pump of claim 1, wherein an inner diameter of the tubular hose is greater than 2.2 millimeters.

7. The infusion pump of claim 1, wherein the second distal core-end comprises a first core-flange and wherein the second distal bladder-end comprises a bladder-shoulder operative to engage the first core-flange.

8. The infusion pump of claim 7, wherein the second distal core-end comprises a second core-flange, wherein the ring member comprises a first distal ring-end and a second distal ring-end, and wherein the second distal ring-end compressively abuts the second core-flange thereby applying a compressive force, via the first distal ring-end, on the bladder-shoulder to further sealingly secure the bladder member to the core member.

9. The infusion pump of claim 8, wherein the first distal ring-end comprises a ring-shoulder operative to engage the bladder-shoulder to further sealingly secure the bladder member to the core member.

10. The infusion pump of claim 1, further comprising a cap, wherein the second distal core-end comprises a third core-flange, and wherein the cap comprises a first cap-flange operative to engage the third core-flange.

11. The infusion pump of claim 1, further comprising a connector tube wherein the connector tube comprises a check valve, a first distal tube-end, and a second distal tube-end, wherein the first distal tube-end is releasably coupled with the second distal hose-end.

12. The infusion pump of claim 1, further comprising a protective cover enveloping the bladder member.

13. A method of injecting, storing, and ejecting a fluid via an infusion pump, comprising:
   (a) providing a core member comprising:
   (i) a substantially spheroidal first distal core-end;
   (ii) a substantially cylindrical second distal core-end; and
   (iii) an infusion port;
   (b) providing a substantially tubular bladder member comprising:
   (i) a substantially spheroidal first distal bladder-end; and
   (ii) a substantially cylindrical open second distal bladder-end operative to receive the core member;
   wherein the core member is disposed inside the bladder member;
   (c) providing a ring member operative to engage the second distal core-end and the second distal bladder-end to sealingly secure the bladder member to the core member; and
   (d) providing a substantially tubular hose comprising a first distal hose-end and a second distal hose-end, wherein the first distal hose-end is coupled with the infusion port;
   whereby injecting a fluid into the infusion pump via the tubular hose inflates the bladder member and stores the fluid substantially symmetrically within the bladder member and the core member around an axial axis of the core member; and
   whereby allowing the bladder member to deflate ejects the fluid out of the infusion pump via the tubular hose at a substantially constant flow rate.

14. The method of claim 13, wherein the bladder member inflates into a substantially spherical shape when the fluid is stored within the bladder member and the core member.

15. The method of claim 13, further comprising providing a cap, wherein the second distal core-end comprises a third core-flange, and wherein the cap comprises a first cap-flange operative to engage the third core-flange.

16. The method of claim 13, further comprising providing a connector tube wherein the connector tube comprises a check valve, a first distal tube-end, and a second distal tube-end, wherein the first distal tube-end is releasably coupled with the second distal hose-end.

17. The method of claim 13, further comprising providing a protective cover enveloping the bladder member.

* * * * *